(12) United States Patent
Spilker et al.

(10) Patent No.: US 11,107,587 B2
(45) Date of Patent: *Aug. 31, 2021

(54) METHOD FOR TUNING PATIENT-SPECIFIC CARDIOVASCULAR SIMULATIONS

(75) Inventors: Ryan Leonard Spilker, Stanford, CA (US); Charles Anthony Taylor, Jr., Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 13/464,452

(22) Filed: May 4, 2012

(65) Prior Publication Data

US 2012/0259608 A1    Oct. 11, 2012

Related U.S. Application Data

(63) Continuation of application No. 12/219,398, filed on Jul. 21, 2008, now Pat. No. 8,200,466.

(51) Int. Cl.
*G16H 50/50* (2018.01)

(52) U.S. Cl.
CPC .................................. *G16H 50/50* (2018.01)

(58) Field of Classification Search
None
See application file for complete search history.

(56) References Cited

U.S. PATENT DOCUMENTS

| | | | |
|---|---|---|---|
| 4,821,735 A | 4/1989 | Goor et al. | |
| 4,945,478 A | 7/1990 | Merickel et al. | |
| 5,119,816 A | 6/1992 | Gevins | |
| 5,151,856 A | 9/1992 | Halmann et al. | |
| 5,205,289 A | 4/1993 | Hardy et al. | |
| 5,235,510 A | 8/1993 | Yamada et al. | |
| 5,582,173 A | 12/1996 | Li | |
| 5,682,886 A | 11/1997 | Delp et al. | |
| 5,687,208 A | 11/1997 | Bae et al. | |
| 5,687,737 A | 11/1997 | Branham et al. | |
| 5,729,670 A | 3/1998 | Strumolo et al. | |
| 5,740,802 A | 4/1998 | Nafis et al. | |
| 5,782,762 A | 7/1998 | Vining | |
| 5,825,908 A | 10/1998 | Pieper et al. | |
| 5,871,018 A | 2/1999 | Delp et al. | |
| 5,920,319 A | 7/1999 | Vining et al. | |
| 5,947,899 A | 9/1999 | Winslow et al. | |
| 6,026,173 A | 2/2000 | Svenson et al. | |
| 6,047,080 A | 4/2000 | Chen et al. | |
| 6,083,162 A | 7/2000 | Vining | |
| 6,117,087 A * | 9/2000 | Kamm et al. | 600/504 |
| 6,169,917 B1 | 1/2001 | Masotti et al. | |
| 6,176,838 B1 | 1/2001 | Sase | |
| 6,236,878 B1 * | 5/2001 | Taylor et al. | 600/416 |
| 6,272,366 B1 | 8/2001 | Vining | |
| 6,278,460 B1 | 8/2001 | Myers et al. | |
| 6,352,509 B1 | 3/2002 | Kawagishi et al. | |
| 6,366,800 B1 | 4/2002 | Vining et al. | |
| 6,379,041 B1 | 4/2002 | Schuetz et al. | |
| 6,381,562 B2 | 4/2002 | Keane | |
| 6,408,201 B1 | 6/2002 | Foo et al. | |
| 6,442,235 B2 | 8/2002 | Koppe et al. | |
| 6,466,205 B2 | 10/2002 | Simpson et al. | |
| 6,471,656 B1 | 10/2002 | Shalman et al. | |
| 6,478,735 B1 | 11/2002 | Pope et al. | |
| 6,487,432 B2 | 11/2002 | Slack | |
| 6,500,117 B1 | 12/2002 | Hancock, Jr. | |
| 6,501,848 B1 | 12/2002 | Carroll et al. | |
| 6,503,202 B1 | 1/2003 | Hossack et al. | |
| 6,507,753 B1 | 1/2003 | Xue et al. | |
| 6,606,091 B2 | 8/2003 | Liang et al. | |
| 6,628,743 B1 | 9/2003 | Drummond et al. | |
| 6,650,724 B2 | 11/2003 | Strobel | |

(Continued)

FOREIGN PATENT DOCUMENTS

| CN | 1600268 A | 3/2005 |
|---|---|---|
| CN | 201015590 Y | 2/2008 |

(Continued)

OTHER PUBLICATIONS

Spilker et al. Annals of Biomedical Engineering, vol. 35, No. 4, Apr. 2007, pp. 546-559.*

Deschamps et al. International Congress Series 1268 (2004) 75-80.*

Figueroa et al. Computer Methods in Biomechanics and Biomedical Engineering, 2006. https://www.scorec.rpi.edu/REPORTS/2006-24.pdf.*

Spilker, Ryan L., and Charles A. Taylor. "Tuning multidomain hemodynamic simulations to match physiological measurements." Annals of biomedical engineering 38.8 (2010): 2635-2648.

Pennati, Giancarlo, et al. "Computational fluid dynamics models and congenital heart diseases." Frontiers in pediatrics 1 (2013).

Al-Saadi N., et al., "Noninvasive Detection of Myocardial Ischemia from Perfusion Reserve Based on Cardiovascular Magnetic Resonance," Circulation, 2000, vol. 101 (12), pp. 1379-1383.

Anderson H.V., et al., "Coronary Artery Flow Velocity is Related to Lumen Area and Regional Left Ventricular Mass," Circulation, 2000, vol. 102 (1), pp. 48-54.

(Continued)

*Primary Examiner* — Michael L Borin (74) *Attorney, Agent, or Firm* — Bookoff McAndrews, PLLC (57) ABSTRACT

Computational methods are used to create cardiovascular simulations having desired hemodynamic features. Cardiovascular modeling methods produce descriptions of blood flow and pressure in the heart and vascular networks. Numerical methods optimize and solve nonlinear equations to find parameter values that result in desired hemodynamic characteristics including related flow and pressure at various locations in the cardiovascular system, movements of soft tissues, and changes for different physiological states. The modeling methods employ simplified models to approximate the behavior of more complex models with the goal of to reducing computational expense. The user describes the desired features of the final cardiovascular simulation and provides minimal input, and the system automates the search for the final patient-specific cardiovascular model.

25 Claims, 1 Drawing Sheet

(56) References Cited

U.S. PATENT DOCUMENTS

| | | |
|---|---|---|
| 6,666,820 B1 | 12/2003 | Poole |
| 6,694,163 B1 | 2/2004 | Vining |
| 6,711,433 B1 | 3/2004 | Geiger et al. |
| 6,718,004 B2 | 4/2004 | Cesmeli |
| 6,720,966 B2 | 4/2004 | Barth et al. |
| 6,793,496 B2 | 9/2004 | Edic et al. |
| 6,801,643 B2 | 10/2004 | Pieper |
| 6,887,207 B2 | 5/2005 | Hettrick |
| 6,898,453 B2 | 5/2005 | Lee |
| 6,909,913 B2 | 6/2005 | Vining |
| 6,932,842 B1 | 8/2005 | Litschko et al. |
| 6,950,689 B1 | 9/2005 | Willis et al. |
| 6,996,262 B2 | 2/2006 | Li |
| 7,006,955 B2 | 2/2006 | Daft et al. |
| 7,121,832 B2 | 10/2006 | Hsieh et al. |
| 7,149,333 B2 | 12/2006 | Pieper et al. |
| 7,149,564 B2 | 12/2006 | Vining et al. |
| 7,182,602 B2 | 2/2007 | Lakin et al. |
| 7,191,110 B1 * | 3/2007 | Charbel et al. ............... 703/11 |
| 7,229,412 B2 | 6/2007 | Jacob et al. |
| 7,286,866 B2 | 10/2007 | Okerlund et al. |
| 7,302,286 B2 | 11/2007 | Camus et al. |
| 7,321,677 B2 | 1/2008 | Evron et al. |
| 7,327,862 B2 | 2/2008 | Murphy et al. |
| 7,333,643 B2 | 2/2008 | Murphy et al. |
| 7,333,648 B2 | 2/2008 | Edic et al. |
| 7,343,196 B2 | 3/2008 | Okerlund et al. |
| 7,356,367 B2 | 4/2008 | Liang et al. |
| 7,369,691 B2 | 5/2008 | Kondo et al. |
| 7,371,067 B2 | 5/2008 | Anderson et al. |
| 7,462,153 B2 | 12/2008 | Bostian et al. |
| 7,474,776 B2 | 1/2009 | Kaufman et al. |
| 7,505,551 B2 | 3/2009 | Grass et al. |
| 7,526,112 B2 | 4/2009 | Murphy et al. |
| 7,536,042 B2 | 5/2009 | Murphy et al. |
| 7,539,529 B2 | 5/2009 | Schmitt et al. |
| 7,542,595 B2 | 6/2009 | Moreau-Gobard |
| 7,574,026 B2 | 8/2009 | Rasche et al. |
| 7,646,900 B2 | 1/2010 | Movassaghi et al. |
| 7,646,901 B2 | 1/2010 | Murphy et al. |
| 7,650,179 B2 | 1/2010 | Redel et al. |
| 7,657,299 B2 | 2/2010 | Huizenga et al. |
| 7,693,563 B2 | 4/2010 | Suresh et al. |
| 7,725,164 B2 | 5/2010 | Suurmond et al. |
| 7,725,165 B2 | 5/2010 | Chen et al. |
| 7,738,626 B2 | 6/2010 | Weese et al. |
| 7,739,090 B2 | 6/2010 | Charbel et al. |
| 7,742,629 B2 | 6/2010 | Zarkh et al. |
| 7,747,055 B1 | 6/2010 | Vining et al. |
| 7,751,984 B2 | 7/2010 | Tang |
| 7,773,719 B2 | 8/2010 | Galant et al. |
| 7,773,785 B2 | 8/2010 | Murphy et al. |
| 7,792,565 B2 | 9/2010 | Vining |
| 7,792,593 B2 | 9/2010 | Rahn et al. |
| 7,805,177 B2 | 9/2010 | Chen et al. |
| 7,813,785 B2 | 10/2010 | Okerlund et al. |
| 7,853,310 B2 | 12/2010 | Vining et al. |
| 8,157,742 B2 | 4/2012 | Taylor |
| 8,315,812 B2 | 11/2012 | Taylor |
| 8,321,150 B2 | 11/2012 | Taylor |
| 8,366,629 B2 | 2/2013 | Bardy |
| 8,447,552 B2 | 5/2013 | Abraham-Fuchs et al. |
| 8,731,968 B1 | 5/2014 | Iliff |
| 8,831,320 B2 | 9/2014 | Bernhardt et al. |
| 9,002,091 B2 | 4/2015 | Bernhardt et al. |
| 9,323,887 B2 | 4/2016 | Bernhardt et al. |
| 9,405,996 B2 | 8/2016 | Ionasec et al. |
| 2002/0002447 A1 | 1/2002 | Keane |
| 2002/0035458 A1 | 3/2002 | Kim et al. |
| 2002/0052553 A1 | 5/2002 | Shalman et al. |
| 2002/0118869 A1 | 8/2002 | Knoplioch et al. |
| 2002/0120431 A1 | 8/2002 | Keane |
| 2002/0168618 A1 | 11/2002 | Anderson et al. |
| 2003/0023266 A1 | 1/2003 | Borillo et al. |
| 2003/0083582 A1 | 5/2003 | Hirsh |
| 2003/0123606 A1 | 7/2003 | Mollus et al. |
| 2003/0204160 A1 | 10/2003 | Kamm et al. |
| 2004/0034309 A1 | 2/2004 | Pullan et al. |
| 2004/0044282 A1 | 3/2004 | Mixon et al. |
| 2004/0049115 A1 | 3/2004 | Murphy et al. |
| 2004/0064298 A1 | 4/2004 | Levine |
| 2004/0153128 A1 | 8/2004 | Suresh et al. |
| 2005/0010105 A1 | 1/2005 | Sra |
| 2005/0018885 A1 | 1/2005 | Chen et al. |
| 2005/0043609 A1 | 2/2005 | Murphy et al. |
| 2005/0059876 A1 | 3/2005 | Krishnan et al. |
| 2005/0064416 A1 | 3/2005 | Fishman et al. |
| 2005/0131663 A1 | 6/2005 | Bangs et al. |
| 2005/0169420 A1 | 8/2005 | Edic et al. |
| 2005/0249717 A1 | 11/2005 | Burgard et al. |
| 2005/0272992 A1 | 12/2005 | O'Donnell et al. |
| 2006/0069318 A1 | 3/2006 | Keaveny et al. |
| 2006/0142984 A1 | 6/2006 | Weese et al. |
| 2006/0149522 A1 | 7/2006 | Tang |
| 2006/0166176 A1 | 7/2006 | Lakin et al. |
| 2006/0171585 A1 | 8/2006 | Rinck et al. |
| 2006/0235669 A1 | 10/2006 | Charbel et al. |
| 2006/0239524 A1 | 10/2006 | Desh et al. |
| 2006/0239528 A1 | 10/2006 | Camus et al. |
| 2006/0241445 A1 | 10/2006 | Altmann et al. |
| 2006/0241461 A1 | 10/2006 | White et al. |
| 2006/0253024 A1 | 11/2006 | Altmann et al. |
| 2006/0278245 A1 | 12/2006 | Gan |
| 2007/0014452 A1 | 1/2007 | Suresh et al. |
| 2007/0015996 A1 | 1/2007 | Camus et al. |
| 2007/0078325 A1 | 4/2007 | Fuimaono et al. |
| 2007/0078352 A1 | 4/2007 | Pijls et al. |
| 2007/0135707 A1 | 6/2007 | Redel et al. |
| 2007/0163353 A1 | 7/2007 | Lec et al. |
| 2007/0219448 A1 | 9/2007 | Seip et al. |
| 2007/0231779 A1 | 10/2007 | Santhanam et al. |
| 2007/0232883 A1 | 10/2007 | Ilegbusi |
| 2007/0238999 A1 | 10/2007 | Specht |
| 2007/0276214 A1 | 11/2007 | Dachille et al. |
| 2007/0293936 A1 | 12/2007 | Dobak, III |
| 2008/0004508 A1 | 1/2008 | Sun et al. |
| 2008/0020362 A1 | 1/2008 | Cotin et al. |
| 2008/0040087 A1 | 2/2008 | Watrous |
| 2008/0044069 A1 | 2/2008 | Dugal |
| 2008/0051660 A1 | 2/2008 | Kakadaris et al. |
| 2008/0058642 A1 | 3/2008 | Gould |
| 2008/0069419 A1 | 3/2008 | Farag et al. |
| 2008/0097210 A1 | 4/2008 | Salgo et al. |
| 2008/0118121 A1 | 5/2008 | Skinner et al. |
| 2008/0118122 A1 | 5/2008 | Sirohey et al. |
| 2008/0133040 A1 | 6/2008 | Boyden et al. |
| 2008/0177172 A1 | 7/2008 | John et al. |
| 2008/0205722 A1 | 8/2008 | Schaefer et al. |
| 2008/0208068 A1 | 8/2008 | Robertson et al. |
| 2008/0212857 A1 | 9/2008 | Pfister et al. |
| 2008/0221442 A1 | 9/2008 | Tolkowsky et al. |
| 2008/0228086 A1 | 9/2008 | Ilegbusi et al. |
| 2008/0262346 A1 | 10/2008 | Assis et al. |
| 2008/0262814 A1 | 10/2008 | Zheng et al. |
| 2008/0269611 A1 | 10/2008 | Pedrizzetti et al. |
| 2008/0270095 A1 | 10/2008 | Lombaert et al. |
| 2008/0275336 A1 | 11/2008 | Deschamps et al. |
| 2008/0278492 A1 | 11/2008 | Ruijters et al. |
| 2008/0287812 A1 | 11/2008 | Parlikar et al. |
| 2008/0294038 A1 | 11/2008 | Weese et al. |
| 2008/0317310 A1 | 12/2008 | Suresh et al. |
| 2008/0319308 A1 | 12/2008 | Tang |
| 2009/0005672 A1 | 1/2009 | Sugiura |
| 2009/0008830 A1 | 1/2009 | Okazaki et al. |
| 2009/0012382 A1 | 1/2009 | Dutta et al. |
| 2009/0016483 A1 | 1/2009 | Kawasaki et al. |
| 2009/0028289 A1 | 1/2009 | Tsuyuki et al. |
| 2009/0054774 A1 | 2/2009 | Njemanze |
| 2009/0074267 A1 | 3/2009 | Pedrizzetti et al. |
| 2009/0077681 A1 | 3/2009 | Fishman et al. |
| 2009/0088830 A1 | 4/2009 | Mohamed et al. |
| 2009/0097731 A1 | 4/2009 | Sanada et al. |
| 2009/0116715 A1 | 5/2009 | Bredno et al. |
| 2009/0156933 A1 | 6/2009 | Gerard et al. |

(56) References Cited

U.S. PATENT DOCUMENTS

| | | |
|---|---|---|
| 2009/0161938 A1 | 6/2009 | Shekhar et al. |
| 2009/0177454 A1 | 7/2009 | Bronstein et al. |
| 2009/0221907 A1 | 9/2009 | Bar-Tal |
| 2009/0244061 A1 | 10/2009 | De et al. |
| 2009/0281423 A1 | 11/2009 | Sirohey et al. |
| 2009/0281434 A1 | 11/2009 | Messerges et al. |
| 2009/0287135 A1 | 11/2009 | Michishita et al. |
| 2009/0292206 A1 | 11/2009 | Sato |
| 2009/0292349 A1 | 11/2009 | Golesworthy |
| 2009/0292557 A1 | 11/2009 | Sirohey et al. |
| 2009/0310840 A1 | 12/2009 | Mohamed et al. |
| 2009/0322749 A1 | 12/2009 | Kassab et al. |
| 2009/0324052 A1 | 12/2009 | Nowinski et al. |
| 2010/0002925 A1 | 1/2010 | Kiraly et al. |
| 2010/0010787 A1 | 1/2010 | Suematsu et al. |
| 2010/0017171 A1 | 1/2010 | Spilker et al. |
| 2010/0041981 A1 | 2/2010 | Kassab |
| 2010/0053209 A1 | 3/2010 | Rauch et al. |
| 2010/0067760 A1 | 3/2010 | Zhang et al. |
| 2010/0070249 A1 | 3/2010 | Ionasec et al. |
| 2010/0081917 A1 | 4/2010 | Zhang et al. |
| 2010/0086099 A1 | 4/2010 | Kuzmanovic |
| 2010/0121178 A1 | 5/2010 | Krishnan, Sr. et al. |
| 2010/0125197 A1 | 5/2010 | Fishel |
| 2010/0130878 A1 | 5/2010 | Lasso et al. |
| 2010/0152570 A1 | 6/2010 | Navab |
| 2010/0156898 A1 | 6/2010 | Voros et al. |
| 2010/0172554 A1 | 7/2010 | Kassab et al. |
| 2010/0183206 A1 | 7/2010 | Carlsen et al. |
| 2010/0189337 A1 | 7/2010 | Jandt et al. |
| 2010/0241404 A1 | 9/2010 | Taylor et al. |
| 2010/0265251 A1 | 10/2010 | Vining et al. |
| 2010/0266176 A1 | 10/2010 | Masumoto et al. |
| 2010/0272315 A1 | 10/2010 | Tsin et al. |
| 2010/0278405 A1 | 11/2010 | Kakadiaris et al. |
| 2010/0280352 A1 | 11/2010 | Ionasec et al. |
| 2010/0298719 A1 | 11/2010 | Kock et al. |
| 2010/0299077 A1 | 11/2010 | Kassab et al. |
| 2010/0328305 A1 | 12/2010 | Vining |
| 2011/0060576 A1 | 3/2011 | Sharma et al. |
| 2011/0071404 A1 | 3/2011 | Schmitt et al. |
| 2011/0085977 A1 | 4/2011 | Rosenmeier |
| 2011/0131167 A1 | 6/2011 | Achterberg |
| 2011/0144920 A1 | 6/2011 | McGregor et al. |
| 2011/0152599 A1 | 6/2011 | Bokeriya et al. |
| 2011/0178383 A1 | 7/2011 | Kassab |
| 2011/0178417 A1 | 7/2011 | Kassab |
| 2011/0275934 A1 | 11/2011 | Kassab |
| 2011/0275936 A1 | 11/2011 | Cho et al. |
| 2011/0282586 A1 | 11/2011 | Kassab et al. |
| 2012/0022843 A1 | 1/2012 | Ionasec et al. |
| 2012/0041318 A1 | 2/2012 | Taylor |
| 2012/0041319 A1 | 2/2012 | Taylor et al. |
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041735 A1 | 2/2012 | Taylor |
| 2012/0041739 A1 | 2/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0072190 A1 | 3/2012 | Sharma et al. |
| 2012/0072193 A1 | 3/2012 | De |
| 2012/0084064 A1 | 4/2012 | Dzenis et al. |
| 2012/0121151 A1 | 5/2012 | Bernhardt et al. |
| 2012/0122777 A1 | 5/2012 | Daimon et al. |
| 2012/0150516 A1 | 6/2012 | Taylor et al. |
| 2012/0243761 A1 | 9/2012 | Senzig et al. |
| 2013/0060133 A1 | 3/2013 | Kassab et al. |
| 2013/0090555 A1 | 4/2013 | Kassab |
| 2013/0132054 A1 | 5/2013 | Sharma et al. |
| 2013/0197884 A1 | 8/2013 | Mansi et al. |
| 2013/0226003 A1 | 8/2013 | Edic et al. |
| 2013/0246034 A1 | 9/2013 | Sharma et al. |
| 2013/0324842 A1 | 12/2013 | Mittal et al. |
| 2014/0029835 A1 | 1/2014 | Kim et al. |
| 2014/0073976 A1 | 3/2014 | Fonte et al. |
| 2014/0148693 A1 | 5/2014 | Taylor |
| 2014/0200867 A1 | 7/2014 | Lavi et al. |
| 2014/0243663 A1 | 8/2014 | Taylor |
| 2014/0249399 A1 | 9/2014 | Sharma et al. |
| 2015/0065864 A1 | 3/2015 | Sharma et al. |
| 2015/0112191 A1 | 4/2015 | Gilboa et al. |
| 2015/0265162 A1 | 9/2015 | Lavi et al. |
| 2015/0297161 A1 | 10/2015 | Grass et al. |
| 2015/0342551 A1 | 12/2015 | Lavi et al. |
| 2015/0356734 A1 | 12/2015 | Ooga et al. |
| 2016/0022371 A1 | 1/2016 | Sauer et al. |

FOREIGN PATENT DOCUMENTS

| | | |
|---|---|---|
| CN | 101172042 A | 5/2008 |
| EP | 0559919 A1 | 9/1993 |
| EP | 1125548 A1 | 8/2001 |
| EP | 1182619 A2 | 2/2002 |
| EP | 1225541 A2 | 7/2002 |
| EP | 1482470 A2 | 12/2004 |
| EP | 1492071 A1 | 12/2004 |
| EP | 0961993 B1 | 2/2005 |
| EP | 1717758 A2 | 11/2006 |
| EP | 1717759 A1 | 11/2006 |
| EP | 1961384 A1 | 8/2008 |
| EP | 1967140 A1 | 9/2008 |
| EP | 2028606 A1 | 2/2009 |
| EP | 2028608 A2 | 2/2009 |
| EP | 2138091 A1 | 12/2009 |
| EP | 2278597 A1 | 1/2011 |
| EP | 2302594 A2 | 3/2011 |
| EP | 2302595 A2 | 3/2011 |
| EP | 2302596 A1 | 3/2011 |
| JP | 2000515789 A | 11/2000 |
| JP | 2002501774 A | 1/2002 |
| JP | 2002513601 A | 5/2002 |
| JP | 2003508152 A | 3/2003 |
| JP | 2003525067 A | 8/2003 |
| JP | 2004528858 A | 9/2004 |
| JP | 2006230482 A | 9/2006 |
| JP | 2007135894 A | 6/2007 |
| JP | 2007517633 A | 7/2007 |
| JP | 2008009841 A | 1/2008 |
| JP | 2008126077 A | 6/2008 |
| JP | 2009515584 A | 4/2009 |
| JP | 2009523818 A | 6/2009 |
| JP | 2009195586 A | 9/2009 |
| JP | 2009540767 A | 11/2009 |
| JP | 2010115317 A | 5/2010 |
| JP | 2011040055 A | 2/2011 |
| JP | 2012501218 A | 1/2012 |
| JP | 2013505782 A | 2/2013 |
| KR | 20070026135 A | 3/2007 |
| KR | 20070120957 A | 12/2007 |
| KR | 20090093877 A | 9/2009 |
| KR | 20090098839 A | 9/2009 |
| WO | WO-9408315 A1 | 4/1994 |
| WO | WO-9526682 A1 | 10/1995 |
| WO | WO-9638815 A1 | 12/1996 |
| WO | WO-9641567 A2 | 12/1996 |
| WO | WO-9717894 A1 | 5/1997 |
| WO | WO-9749065 A1 | 12/1997 |
| WO | WO-9804182 A2 | 2/1998 |
| WO | WO-9811524 A1 | 3/1998 |
| WO | WO-9832371 A1 | 7/1998 |
| WO | WO-9843201 A1 | 10/1998 |
| WO | WO-9938433 A1 | 8/1999 |
| WO | WO-9942977 A1 | 8/1999 |
| WO | WO-9956612 A1 | 11/1999 |
| WO | WO-9963887 A1 | 12/1999 |
| WO | WO-0007501 A1 | 2/2000 |
| WO | WO-0032106 A1 | 6/2000 |
| WO | WO-0053081 A1 | 9/2000 |
| WO | WO-0055812 A1 | 9/2000 |
| WO | WO-0055814 A2 | 9/2000 |

(56) References Cited

FOREIGN PATENT DOCUMENTS

| | | |
|---|---|---|
| WO | WO-0068749 A1 | 11/2000 |
| WO | WO-0072272 A1 | 11/2000 |
| WO | WO-0117456 A1 | 3/2001 |
| WO | WO-0122362 A1 | 3/2001 |
| WO | WO-0185030 A1 | 11/2001 |
| WO | WO-0229758 A2 | 4/2002 |
| WO | WO-0229764 A1 | 4/2002 |
| WO | WO-02095686 A1 | 11/2002 |
| WO | WO-03034336 A2 | 4/2003 |
| WO | WO-03060553 A2 | 7/2003 |
| WO | WO-03081529 A1 | 10/2003 |
| WO | WO-2004010374 A2 | 1/2004 |
| WO | WO-2004012152 A2 | 2/2004 |
| WO | WO-2004066807 A2 | 8/2004 |
| WO | WO-2004068406 A2 | 8/2004 |
| WO | WO-2004072903 A2 | 8/2004 |
| WO | WO-2005004038 A1 | 1/2005 |
| WO | WO-2005004721 A1 | 1/2005 |
| WO | WO-2005027765 A1 | 3/2005 |
| WO | WO-2005031635 A1 | 4/2005 |
| WO | WO-2005083633 A2 | 9/2005 |
| WO | WO-2005119578 A2 | 12/2005 |
| WO | WO-2006002353 A2 | 1/2006 |
| WO | WO-2006020920 A2 | 2/2006 |
| WO | WO-2006061815 A1 | 6/2006 |
| WO | WO-2006066122 A2 | 6/2006 |
| WO | WO-2006079042 A2 | 7/2006 |
| WO | WO-2006082558 A2 | 8/2006 |
| WO | WO-2007020555 A2 | 2/2007 |
| WO | WO-2007066249 A2 | 6/2007 |
| WO | WO-2007102858 A1 | 9/2007 |
| WO | WO-2007146930 A2 | 12/2007 |
| WO | WO-2008030192 A1 | 3/2008 |
| WO | WO-2009007910 A2 | 1/2009 |
| WO | WO-2009056147 A1 | 5/2009 |
| WO | WO-2010020933 A2 | 2/2010 |
| WO | WO-2010033971 A1 | 3/2010 |
| WO | WO-2010061335 A1 | 6/2010 |
| WO | WO-2010086810 A1 | 8/2010 |
| WO | WO-2011015822 A1 | 2/2011 |
| WO | WO-2011038044 A2 | 3/2011 |
| WO | WO-2012021307 A2 | 2/2012 |

OTHER PUBLICATIONS

Antiga L., et al., "An Image-Based Modeling Framework for Patient-Specific Computational Hemodynamics," Medical & Biological Engineering & Computing, Nov. 2008, vol. 46 (11), pp. 1097-1112.
Arkilic E.B., et al., "Mass Flow and Tangential Momentum Accommodation in Silicon Micromachined Channels," Journal of Fluid Mechanics, 2001, vol. 437, pp. 29-43.
Benson L.N., et al., "Percutaneous Implantation of a Balloon-Expandable Endoprosthesis for Pulmonary Artery Stenosis: An Experimental Study," Journal of the American College of Cardiology, 1991, vol. 18 (5), pp. 1303-1308.
Bernhard S., et al., "Transient Integral Boundary Layer Method to Calculate the Translesional Pressure Drop and the Fractional Flow Reserve in Myocardial Bridges," BioMedical Engineering OnLine, 2006, vol. 5, p. 42.
Berry J.L., et al., "Experimental and Computational Flow Evaluation of Coronary Stents," Annals of Biomedical Engineering, 2000, vol. 28 (4), pp. 386-398.
Bishop A.H., et al., "Fractional Flow Reserve Critical Review of an Important Physiological Adjunct to Angiography," American Heart Journal, 2004, vol. 147 (5), pp. 792-802.
Botman K.J., et al., "Percutaneous Coronary Intervention or ByPass Surgery in Multivessel Disease: A tailored approach based on Coronary Pressure Measurement," Catheterization and Cardiovascular Interventions, 2004, vol. 63 (2), pp. 184-191.
Bottcher M., et al., "Effect of Oral Nitroglycerin and Cold Stress on Myocardial Perfusion in Areas Subtended by Stenosed and Nonstenosed Coronary Arteries," American Journal of Cardiology, 2002, vol. 89 (9), pp. 1019-1024.
Boutsianis E., et al., "Computational Simulation of Intracoronary Flow Based on Real Coronary Geometry," European Journal of Cardio-thoracic Surgery, 2004, vol. 26 (2), pp. 248-256.
Byorigaku-Rinsho, Rubin Igaku heno Kiban—translated as Pathology-Foundation for Clinical Medicine (published on Nov. 6, 2007), Emanuel Rubin Ed, Toshimitsu Suzuki, Hideo Nakamura, Masahisa Fukayama, Mitsutoku Yamakawa, Tadashi Yoshino(translation supervisor), Nishimura Co, Ltd, pp. 426-432.
Chambers J., et al., "The Peak to Mean Pressure Decrease Ratio: A New Method of Assessing Aortic Stenosis," Journal of the American Society of Echocardiography, 2005, vol. 18 (6), pp. 674-678.
Chen S., et al., "Lattice Boltzmann Method for Fluid Flows," Annual Review of Fluid Mechanics, 1998, vol. 30, pp. 329-364.
Choy J.S., et al., "Scaling of Myocardial Mass to Flow and Morphometry of Coronary Arterie," Journal of Applied Physiology, 2008, vol. 104 (5), pp. 1281-1286.
Cilla M., et al., "Machine Learning Techniques as a Helpful Tool Toward Determination of Plaque Vulnerability," IEEE Transactions on Biomedical Engineering, 2012, vol. 59 (4), pp. 1155-1161.
De Bruyne B., et al., "Simultaneous Coronary Pressure and Flow Velocity Measurements in Humans. Feasibility, Reproducibility, and Hemodynamic Dependence of Coronary Flow Velocity Reserve, Hyperemic Flow Versus Pressure Slope Index, and Fractional Flow Reserve," Circulation, 1996, vol. 94 (8), pp. 1842-1849.
Ellwein L.M., et al., "Sensitivity Analysis and Model Assessment: Mathematical Models for Arterial Blood Flow and Blood Pressure," Cardiovascular Engineering, 2008, vol. 8 (2), pp. 94-108.
Erglis A., et al., "Non-invasive FFR Using Coronary CT Angiography and Computational Fluid Dynamics Predicts the Hemodynamic Significance of Coronary Lesions," 2010, 19 pages.
European Search Report for Application No. EP14189381, dated Feb. 16, 2015, 8 pages.
European Search Report for Application No. EP15178021, dated Oct. 30, 2015, 8 pages.
European Search Report for Application No. EP17155303, dated May 24, 2017, 7 pages.
Final Office Action dated May 1, 2012 for U.S. Appl. No. 13/290,842, filed Nov. 7, 2011.
Final Office Action dated Jul. 3, 2012 for U.S. Appl. No. 13/290,641, filed Nov. 7, 2011.
Final Office Action dated Jun. 29, 2012 for U.S. Appl. No. 13/013,561, filed Jan. 25, 2011.
Formaggia L., et al., "Numerical Treatment of Defective Boundary Conditions for the Navier-Stokes Equations," SIAM Journal on Numerical Analysis, 2002, vol. 40 (1), pp. 376-401.
Forster S., et al., "Tc-99m Sestamibi Single Photon Emission Computed Tomography for Guiding Percutaneous Coronary Intervention in Patients with Multivessel Disease: A Comparison with Quantitative Coronary Angiography and Fractional Flow Reserve," The International Journal of Cardiovascular Imaging, 2010, vol. 26 (2), pp. 203-213.
Frauenfelder T., et al., "In-vivo Flow Simulation in Coronary Arteries Based on Computed Tomography Data Sets: Feasibility and Initial Results," European Radiology, 2007, vol. 17 (5), pp. 1291-1300.
Gijsen F.J., et al., "Strain Distribution Over Plaques in Human Coronary Arteries Relates to Shear Stress," The American Journal of Physiology-Heart and Circulatory Physiology, 2008, vol. 295 (4), pp. H1608-H1614.
Hamada M., et al., "Shinkakudai No Hasseikijyo (Mechanism of Development of Heart Enlargement)," Modern Physician, Shinkoh-IgakuShuppan Co. Ltd, 1997, vol. 17 (8), pp. 967-970.
Himeno R., et al., "Blood Flow Simulation and its application to Medical Treatment," Journal of the Japan Society of Precision Engineering, 2005, vol. 71 (4), pp. 427-430.
Kassab G.S., et al., "Morphometry of Pig Coronary Arterial Trees," American Journal of Physiology, 1993, vol. 265, pp. H350-H365.
Kim., et al., "Three-Dimensional Finite Element Modeling of Blood Flow in the Coronary Arteries," World Congress on Computational Mechanics, 2008.

(56) References Cited

OTHER PUBLICATIONS

Kim H.J., et al., "On Coupling a Lumped Parameter Heart Model and a Three-Dimensional Finite Element Aorta Model," Annals of Biomedical Engineering, 2009, vol. 37 (11), pp. 2153-2169.
Kim H.J., et al., "Patient-Specific Modeling of Blood Flow and Pressure in Human Coronary Arteries," Annals of Biomedical Engineering, 2010, vol. 38 (10), pp. 3195-3209.
Kock S.A., et al., "Mechanical Stresses in Carotid Plaques using MRI-Based Fluid-Structure Interaction Models," Journal of Biomechanics, 2008, vol. 41 (8), pp. 1651-1658.
Kristensen T.S., et al., "Correlation Between Coronary Computed Tomographic Angiography and Fractional Flow Reserve," International Journal of Cardiology, 2010, vol. 144 (2), pp. 200-205.
Ku J.P., et al., "In Vivo Validation of Numerical Prediction of Blood Flow in Arterial Bypass Grafts," Annals of Biomedical Engineering, 2002, vol. 30 (6), pp. 743-752.
Kurita T., et al., "Regional Myocardial Perfusion Reserve Determined Using Myocardial Perfusion Magnetic Resonance Imaging Showed a Direct Correlation With Coronary Flow Velocity Reserve by Doppler Flow Wire," European Heart Journal, 2009, vol. 30 (4), pp. 444-452.
Lagana K., et al., "Multiscale Modeling of the Cardiovascular System: Application to the Study of Pulmonary and Coronary Perfusions in the Univentricular Circulation," Journal of Biomechanics, 2005, vol. 38 (5), pp. 1129-1141.
Latifoglu F., et al., "Medical Diagnosis of Atherosclerosis from Carotid Artery Doppler Signals using Principal Component Analysis (PCA), k-NN based weighting pre-processing and Artificial Immune Recognition system (AIRS)," Journal of Biomedical Informatics, 2008, vol. 41 (1), pp. 15-23.
Le H., et al., "Estimation of Regional Myocardial Mass at Risk Based on Distal Arterial Lumen Volume and Length Using 3d Micro-Ct Images," Computerized Medical Imaging and Graphics, 2008, vol. 32 (6), pp. 488-501.
Lee D.C., et al., "Quantification of Absolute Myocardial Blood Flow by Magnetic Resonance Perfusion Imaging," JACC Cardiovascular Imaging, 2009, vol. 2 (6), pp. 761-770.
Lee K.W., et al., "Ultrasound Image-Based Computer Model of a Common Carotid Artery with a Plaque," Medical Engineering and Physics, 2004, vol. 26 (10), pp. 823-840.
Lesage D., et al., "A Review of 3d Vessel Lumen Segmentation Techniques: Models, Features and Extraction Schemes," Medical Image Analysis, 2009, vol. 13 (6), pp. 819-845.
Leuprecht A., et al., "Blood Flow in the Human Ascending Aorta: a Combined MRI and CFD Study," Journal of Engineering Mathematics, 2003, vol. 47 (3), pp. 387-404.
Li Q., et al., "How to Reconstruct 3D Coronary Arterial Tree from Two Arbitrary Views," Bioinformatics and Biomedical Engineering, 2009.
Lim C.Y., et al., "Application of lattice Boltzmann method to simulate microchannel flows," Physics of Fluids, 2002, vol. 14 (7), pp. 2299-2308.
Liu D., et al., "Computational Analysis of Oxygen Transport in the Retinal Arterial Network," Current Eye Research, 2009, vol. 34 (11), pp. 945-956.
Liu H., et al., "Multi-scale Simulation of Circulatory System," Journal of the Japan Society of Precision Engineering, 2005, vol. 71 (12), pp. 1492-1497.
Marshall W.W., et al., "Use of a Secure Internet Web Site for Collaborative Medical Research," JAMA, 2000, vol. 284 (14), pp. 1843-1849.
Mathematical Optimization, Sep. 30, 2009, Wikipedia,< https://en.wikipedia.org/wiki/Mathematicl.sub.--optimization>.
Melikian N., et al., "Fractional Flow Reserve and Myocardial Perfusion Imaging in Patients with Angiographic Multivessel Coronary Artery Disea," JACC: Cardiovascular Interventions, 2010, vol. 3 (3), pp. 307-314.
Migliavacca F., et al., "Multiscale Modelling in Biofluidynamics: Application to Reconstructive Paediatric Cardiac Surgery, " Journal of Biomechanics, 2006, vol. 39 (6), pp. 1010-1020.
Morris P.D., et al., "Virtual Fractional Flow Reserve from Coronary Angiography: Modeling the Significance of Coronary Lesions: Results From the VIRTU-1 (VIRTUal Fractional Flow Reserve From Coronary Angiography) Study," JACC: Cardiovascular Interventions, 2013, vol. 6 (2), pp. 149-157.
Motoyama S., et al., "Computed Tomographic Angiography Characteristics of Atherosclerotic Plaques Subsequently Resulting in Acute Coronary Syndrome," Journal of the American College of Cardiology, 2009, vol. 54 (1), pp. 49-57.
Myers J.G., et al., "Factors Influencing Blood Flow Patterns in the Human Right Coronary Artery," Annals of Biomedical Engineering, 2001, vol. 29 (2), pp. 109-120.
Nagai H., et al., "Advance in Imaging-Technology for Cardiac Area Analysis," The Institute of Electronics Information and Communication Engineers Technical Report, Iryogazo, 2007, vol. 106 (510), pp. 147-149.
Nagel E., et al., "Magnetic Resonance Perfusion Measurements for the Noninvasive Detection of Coronary Artery Disease," Circulation, 2003, vol. 108 (4), pp. 432-437.
Neal M.L., et al., "Current Progress in Patient-Specific Modeling," Briefings in Bioinformatics, 2010, vol. 11 (1), pp. 111-126.
Non-Final Office Action dated Feb. 3, 2012 for U.S. Appl. No. 13/290,476, filed Nov. 7, 2011.
Non-Final Office Action dated Apr. 4, 2012 for U.S. Appl. No. 12/661,491, filed Mar. 17, 2010.
Non-Final Office Action dated Apr. 8, 2013 for U.S. Appl. No. 13/014,809, filed Jan. 27, 2011.
Non-Final Office Action dated Apr. 11, 2012 for U.S. Appl. No. 13/014,835, filed Jan. 27, 2011.
Non-Final Office Action dated May 11, 2012 for U.S. Appl. No. 13/291,089, filed Nov. 7, 2011.
Non-Final Office Action dated Apr. 12, 2012 for U.S. Appl. No. 13/014,857, filed Jan. 27, 2011.
Non-Final Office Action dated Mar. 13, 2012 for U.S. Appl. No. 13/290,641, filed Nov. 7, 2011.
Non-Final Office Action dated Apr. 16, 2012 for U.S. Appl. No. 13/014,841, filed Jan. 27, 2011.
Non-Final Office Action dated Apr. 18, 2012 for U.S. Appl. No. 13/014,845, filed Jan. 27, 2011.
Non-Final Office Action dated Apr. 19, 2012 for U.S. Appl. No. 13/014,850, filed Jan. 27, 2011.
Non-Final Office Action dated Apr. 22, 2013 for U.S. Appl. No. 13/014,821, filed Jan. 27, 2011.
Non-Final Office Action dated Jun. 22, 2012 for U.S. Appl. No. 13/014,829, filed Jan. 27, 2011.
Non-Final Office Action dated Feb. 23, 2012 for U.S. Appl. No. 13/013,561, filed Jan. 25, 2011.
Non-Final Office Action dated May 25, 2012 for U.S. Appl. No. 13/291,077, filed Nov. 7, 2011.
Non-Final Office Action dated Jan. 26, 2012 for U.S. Appl. No. 13/290,842, filed Nov. 7, 2011.
Ohashi T., et al., "Computational Analysis of the Stress and Strains with in an Atherosclerotic Plaque Exerted by Interaction Between the Blood Flow and the Vessel Wall Structure, Proceedings of the JSME Bioengineering Conference and Seminar," The Japan Society of Mechanical Engineers, 2000, vol. 11, pp. 103-104.
Olufsen M.S., et al., "Modeling Heart Rate Regulation—Part I: Sit-to-Stand Versus Head-Up Tilt," Cardiovascular Engineering—an International Journal, 2008, vol. 8 (2), pp. 73-87.
Olufsen M.S., et al., "On Deriving Lumped Models for Blood Flow and Pressure in the Systemic Arteries," Mathematical Biosciences and Engineering, 2004, vol. 1 (1), pp. 61-80, Retrieved from the Internet: URL:http://www4.ncsu.edu/~msolufse/OlufsenNadim.pdf,[retrieved on Jul. 15, 2015], XP055202425.
Partial European Search Report for Application No. EP14189383, dated May 26, 2015, 8 pages.
Pekkan K., et al., "Patient-Specific Surgical Planning and Hemodynamic Computational Fluid Dynamics Optimization Through Free-Form Haptic Anatomy Editing Tool (SURGEM), " Medical and Biological Engineering and Computing, 2008, vol. 46 (11), pp. 1139-1152.
Pereztol V., et al., "Correspondence Between Left Ventricular 17 Myocardial Segments and Coronary Arteries," European Heart Journal, 2005, vol. 26 (24), pp. 2637-2643.

(56) References Cited

OTHER PUBLICATIONS

Perktold K., et al., "Validated Computation of Physiologic Flow in a Realistic Coronary Artery Branch," Journal of Biomechanics, 1998, vol. 31 (3), pp. 217-228.
Pijls N.H., et al., "Measurement of Fractional Flow Reserve to Assess the Functional Severity of Coronary-Artery Stenoses," New England Journal of Medicine, 1996, vol. 334 (26), pp. 1703-1708.
Pijls N.H., et al., "Percutaneous Coronary Intervention of Functionally Nonsignificant Stenosis: 5-year follow-up of the DEFER Study," Journal of the American College of Cardiology, 2007, vol. 49 (21), pp. 2105-2111.
Pinciroli F., et al., "ARCADIA: A System for the Integration of Angiocardiographic Data and Images by an Object-Oriented DBMS," Computers and Biomedical Research, 1995, vol. 28 (1), pp. 5-23.
Qian Y., et al., "Computational Hemodynamic Analysis in Congenital Heart Disease: Simulation of the Norwood Procedure, "Annals of Biomedical Engineering, 2010, vol. 38 (7), pp. 2302-2313.
Qiu Y., et al., "Numerical Simulation of Pulsatile Flow in a Compliant Curved Tube Model of a Coronary Artery," Journal of Biomechanical Engineering, 2000, vol. 122 (1), pp. 77-85.
Quarteroni A., et al., "Coupling Between Lumped and Distributed Models for Blood Flow Problems," Computing and Visualization in Science, 2001, vol. 4 (2), pp. 111-124.
Quarteroni A., et al., "On the Mathematical Modeling of the Cardiovascular System (Invited Lectures in the 12.sup.th JSIAM Annual Meeting), Bulletin," The Japan Society for Industrial and Applied Mathematics, 2003, vol. 13 (1), pp. 79-82.
Rieber J., et al., "Cardiac Magnetic Resonance Perfusion Imaging for the Functional Assessment of Coronary Artery Disease: A Comparison with Coronary Angiography and Fractional Flow Reserve, " European Heart Journal, 2006, vol. 27 (12), pp. 1465-1471.
Rong T.U., et al., "3D Reconstruction of Coronary Arteries from Two X-ray Angiograms based on Anatomic Model," Proceeding of the International Society for Optics and Photonics, 2007, vol. 6534, 8 page.
Sakamoto A., et al., Hyojun Byorigaku [translated as Standard Pathology] 4th Ed (published on Aug. 1, 2010), Atsuhiko Sakamoto, Masanobu Kitagawa, Toshiro Niki (Ed.), Igaku Shoin Ltd, pp. 324-330.
Sakamoto A., et al., Hyojun Byorigaku [translated as Standard Pathology] 4th Ed (published on Aug. 1, 2010), Atsuhiko Sakamoto, Masanobu Kitagawa, Toshiro Niki (Ed.), Igaku Shoin Ltd, pp. 345-349.
Santamarina A., et al., "Computational Analysis of Flow in a Curved Tube Model of the Coronary Arteries: Effects of Time-Varying Curvature," Annals of Biomedical Engineering, 1998, vol. 26 (6), pp. 944-954.
Schroeder T., et al., "Cerebral Hyperfusion Following Carotid Endarterectomy," Journal of Neurosurgery, 1987, vol. 66 (6), pp. 824-829.
Schwarz S., et al., "Effects of Induced Hypertension on Intracranial Pressure and Flow Velocities of the Middle Cerebral Arteries in Patients with Large Hemispheric Stroke," Stroke, 2002, vol. 33 (4), pp. 998-1004.
Shalman E., et al., "Numerical Modeling of the Flow in Stenosed Coronary Artery. The Relationship Between Main Hemodynamic Parameters," Computers in Biology and Medicine, 2002, vol. 32 (5), pp. 329-344.
Shalman E., et al., "Pressure-based Simultaneous CFR and FFR Measurements: Understanding the Physiology of a Stenosed Vessel," Computers in Biology and Medicine, 2001, vol. 31 (5), pp. 353-363.
Singh P.K., et al., "The Role of Computational Fluid Dynamics in the Management of Unruptured Intracranial Aneurysms: a Clinicians' View," Computational Intelligence and Neuroscience, 2009.
Spilker R.L., Computational Analysis of Blood Flow in Arteriesincorporating Reduced-Order Models of the Downstreamvasculature, Dissertation, Jun. 2009, XP055230855, Retrieved from the Internet: URL:http://search.proquest.com/docview/304999618>.
Spilker R.L., et al., "Models and Methods in Computational Vascular and Cardiovascular Mechanics, 9th U.S. National Congress on Computational Mechanics," 2007, 1 page.
Spilker R.L., et al., "Tuning Hemodynamic Simulations With Three-Element Windkessel Outlet Boundary Conditions," 2007.
Steele B.N., et al., "In vivo Validation of a One-Dimensional Finite-Element Method for Predicting Blood Flow in Cardiovascular Bypass Grafts," IEEE Transactins on Biomedical Engineering, 2003, vol. 50 (6), pp. 649-656.
Steinman D.A., et al., "Flow Imaging and Computing: Large Artery Hemodynamics," Annals of Biomedical Engineering, 2005, vol. 33 (12), pp. 1704-1709.
Steinman D.A., et al., "Image-Based Computational Fluid Dynamics Modeling in Realistic Arterial Geometries," Annals of Biomedical Engineering, 2002, vol. 30 (4), pp. 483-497.
Sud V.K., et al., "Simulation of Steady Cardiovascular Flow in the Presence of Stenosis using a Finite Element Method," Physics in Medicine and Biology, 1990, vol. 35 (7), pp. 947-959.
Suttorp M.J., et al., "Primary Stenting of Totally Occluded Native Coronary Arteries II (PRISON II): a Randomized Comparison of Bare Metal Stent Implantation with Sirolimus-Eluting Stent Implantation for the Treatment of Total Coronary Occlusions," Circulation, 2006, vol. 114 (9), pp. 921-928.
Tang D., et al., "Local Maximal Stress Hypothesis and Computational Plaque Vulnerability Index for Atherosclerotic Plaque Assessment," Annals of Biomedical Engineering, 2005, vol. 33 (12), pp. 1789-1801.
Taylor C.A., et al., "A Computational Framework for Investigating Hemodynamic Factors in Vascular Adaptation and Disease," 1996, 118 pages.
Taylor C.A., et al., "Computational Investigations in Vascular Disease," Computers in Physics, 1996, vol. 10 (3), pp. 224-232.
Taylor C.A., et al., "Image-Based Modeling of Blood Flow and Vessel Wall Dynamics: Applications, Methods and Future Directions: Sixth International Bio-Fluid Mechanics Symposium and Workshop, Mar. 28-30, 2008 Pasadena, California.," Annals of Biomedical Engineering, 2010, vol. 38 (3), pp. 1188-1203.
Taylor C.A., et al., "Open Problems in Computational Vascular Biomechanics: Hemodynamics and Arterial Wall Mechanics," Computer Methods in Applied Mechanics and Engineering, 2009, vol. 198 (45-46), pp. 3514-3523.
Taylor C.A., et al., "Patient-Specific Modeling of Cardiovascular Mechanics," Annual Review of Biomedical Engineering, 2009, vol. 11, pp. 109-134.
Taylor C.A., et al., "Predictive Medicine: Computational Techniques in Therapeutic Decision-Making," Computer Aided Surgery, 1999, vol. 4 (5), pp. 231-247.
Taylor C.A., et al., "The HeartFlow Concept Combining Angiographic Imaging and Non-invasive Hemodynamic Lesion Assessment: Technology Description," Transcatheter Cardiovascular Therapeutics (TCT) Conference, 2010, 12 pages.
Termeer M., et al., "Visualization of Myocardial Perfusion Derived from Coronary Anatomy," IEEE Transactions on Visualization and Computer Graphics, 2008, vol. 14 (6), pp. 1595-1602.
U.S. Appl. No. 61/210,401, Inventor name: Charles A. Taylor et al., Title: Patient-Specific Hemodynamics of the Cardiovascular System, filed Mar. 17, 2009.
Vignon-Clementel I.E., et al., "Outflow Boundary Conditions for Three-Dimensional Finite Element Modeling of Blood Flow and Pressure in Arteries," Computer Methods in Applied Mechanics and Engineering, 2006, vol. 195 (29-32), pp. 3776-3796.
Wang K.C., et al., "Improving Geometric Model Construction for Blood Flow Modeling," IEEE Engineering in Medicine and Biology, 1999, vol. 18 (6), pp. 33-39.
Watkins S., et al., "Validation of Magnetic Resonance Myocardial Perfusion Imaging With Fractional Flow Reserve for the Detection of Significant Coronary Heart Disease," Circulation, 2009, vol. 120, pp. 2207-2213.
Wilson N., et al., "A Software Framework for Creating Patient Specific Geometric Models from Medical Imaging Data for Simulation Based Medical Planning of Vascular Surgery," Medical Image Computing and Computer-Assisted Intervention—MICCAI, 2001, vol. 2208, pp. 449-456.

(56) References Cited

OTHER PUBLICATIONS

Wilson N.M., et al., "An Integrated Software System for Preoperatively Evaluating Aorto-Femoral Reconstruction Procedures," Summer Bioengineering Conference, 2003, pp. 899-900, [retrieved on May 19, 2015]. Retrieved from the Internet< URL: http://www.tulane.eduj-sbc2003/pdfdocs/0899.pdf>.
Wong J.T., et al., "Determination of Fractional Flow Reserve (FFR) based on Scaling Laws: a Simulation Study," Physics in Medicine and Biology, 2008, vol. 53 (14), pp. 3995-4011.
Wood N.B., et al., "Combined MR Imaging and CFD Simulation of Flow in the Human Descending Aorta," Journal of Magnetic Resonance Imaging, 2001, vol. 13 (5), pp. 699-713.
Yao J., et al., "Image-Based Fractional Flow Reserve Using Coronary Angiography," IEEE Nuclear Science Symposium and Medical Imaging Conference, 2013.
Yin W., et al., "3D Numerical Simulation of Coronary Blood Flow and Its Effect on Endothelial Cell Activation," Engineering in Medicine and Biology Society, 2009, pp. 4003-4006.
Yokoi H., et al., "Teiryoteki Kandomyaku Zoei (QCA) no Genjo to Shorai: Translated as Current state and Future of Quantitative Coronary Angiography," Journal of a Measurement Subcommittee, 2001, vol. 9 (1), pp. 14-20.
Zhang J.M., et al., "Perspective on CFD Studies of Coronary Artery Disease Lesions and Hemodynamics: A Review," International Journal for Numerical Methods in Biomedical Engineering, 2014.
Fernandez M.A., et al., "An Exact Block-Newton Algorithm for the Solution of Implicit Time Discretized Coupled Systems Involved in Fluid-Structure Interaction Problems," Computational Fluid and Solid Mechanics, Jun. 17-20, 2003, K.J. Bathe, Editor, Proceedings Second MIT Conference on Computational Fluid and Solid Mechanics, Elsevier Science Ltd, pp. 1337-1341.
Devault K., et al., "Blood Flow in the Circle of Willis: Modeling and Calibration," Multiscale Modeling & Simulation, Jan. 2008, vol. 7 (2), pp. 888-909.
Migliavacca F., et al., "Modeling of the Norwood Circulation: Effects of Shunt Size, Vascular Resistances, and Heart Rate," American Journal of Physiology Heart and Circulatory Physiology, May 2001, vol. 280 (5), pp. H2076-H2086.
Parkes L.M., et al., "Improved Accuracy of Human Cerebral Blood Perfusion Measurements using Arterial Spin Labeling: Accounting for Capillary Water Permeability," Magnetic Resonance in Medicine, Jul. 2002, vol. 48 (1), pp. 27-41.
Formaggia L., et al., "On the Coupling of 3D and 1D Navier-Stokes Equations for Flow Problems in Compliant Vessels," Theme 4 Simulation and Optimization Complex Systems, M3N project, Research Report No. 3862, Jan. 2000, 29 pages.
Jung E., et al., "Lumped Parameter Models of Cardiovascular Circulation in Normal and Arrhythmia Cases," Journal of the Korean Mathematical Society, 2006, vol. 43, pp. 885-897.
Koo B.K., et al., "Diagnosis of Ischemia-Causing Coronary Stenoses by Noninvasive Fractional Flow Reserve Computed from Coronary Computed Tomographic Angiograms. Results from the Prospective Multicenter Discover-Flow (Diagnosis of Ischemia-Causing Stenoses Obtained Via Noninvasive Fractional Flow Reserve) study," Journal of the American College of Cardiology, 2011, vol. 58 (19), pp. 1989-1997.
Shim E.B., et al., "Mathematical Modeling of Cardiovascular System Dynamics Using a Lumped Parameter Method," The Japanese Journal of Physiology, 2004, vol. 54 (6), pp. 545-553.
Yang G.Z., et al., "Flow and Myocardial Interaction: An Imaging Perspective," Philosophical Transactions of the Royal Society of London. Series B, Biological Sciences, Aug. 29, 2007, vol. 362 (1484), pp. 1329-1341.
Napel S., et al., "Visualizing Three-dimensional Flow with Simulated Streamlines and Three-dimensional Phase-contrast MR Imaging," Journal of Magnetic Resonance Imaging, May-Apr. 1992, vol. 2 (2), pp. 143-153.
Sourbron S., et al., "Quantification of Cerebral Blood Flow, Cerebral Blood Volume, and Blood-brain-barrier Leakage with-DCE-MRI," Magnetic Resonance in Medicine, Jul. 2009, vol. 62 (1), pp. 205-217.
David T., et al., "Modeling Perfusion in the Cerebral Vasculature," Medical Engineering & Physics, Dec. 2008, vol. 30 (10), pp. 1227-1245.
Zhao S.Z., et al., "Blood Flow and Vessel Mechanics in a Physiologically Realistic Model of a Human Carotid Arterial Bifurcation", Journal of Biomechanics, Aug. 2000, vol. 33 (8), pp. 975-984.
Caramia et al., "Chapter 2: Multi-Objective Optimization", 2008, Multi-Objective Management in Freight Logistics, Springer, XVI, 187, pp. 11-36.
El Fakhri G., et al., "Quantitative Dynamic Cardiac 82Rb PET Using Generalized Factor and Compartment Analyses," Journal of Nuclear Medicine, Aug. 2005, vol. 46 (8), pp. 1264-1271.
Jerosch-Herold M., et al., "Analysis of Myocardial Perfusion MRI," Journal of Magnetic Resonance Imaging, Jun. 2004, vol. 19 (6), pp. 758-770.
Larsson, H.B., et al., "Measurement of Brain Perfusion, Blood Volume, and Blood-Brain Barrier Permeability, Using Dynamic Contrast-Enhanced T(1)-Weighted MRI at 3 Tesla", Magnetic Resonance in Medicine, Nov. 2009, vol. 62 (5), pp. 1270-1281.
Sermesant M., et al., "Toward Patient-specific Myocardial Models of the Heart," Heart Failure Clinics, Jul. 2008, vol. 4 (3), pp. 289-301.

\* cited by examiner

METHOD FOR TUNING PATIENT-SPECIFIC CARDIOVASCULAR SIMULATIONS

PRIORITY

This application is a continuation of U.S. patent application Ser. No. 12/219,398, filed Jul. 21, 2008, which is herein incorporated by reference in its entirety.

FEDERALLY-SPONSORED RESEARCH OR DEVELOPMENT

This invention was made with Government support under contract 0205741 awarded by the National Science Foundation. The Government has certain rights in this invention.

BACKGROUND OF THE INVENTION

1. Field of the Invention

This invention relates generally to computer-assisted modeling and planning systems and in particular to a computer-assisted human anatomic and physiologic modeling system used to predict outcomes of medical intervention and further to predict changes in physiologic function under various states, stresses, and environments and still further to generate data for disease research or medical device design.

2. Discussion of Prior Art

Disclosed in Kamm et al., U.S. Pat. No. 6,117,087, is a method and apparatus for deriving a physiological description and clinically-useful data regarding the cardiovascular system of an individual subject. The method includes obtaining a measurement sample associated with cardiovascular flow and utilizing a model, which may be distributed and/or non-linear to derive a description and data. The model generates and uses functions of source parameters and may, in an embodiment, match measurement samples against a library of stored, predicted samples. A best-matching, predicted sample may then be associated with a measurement sample. An apparatus is provided that, according to an embodiment, includes an input for obtaining a measurement sample, a processor to derive the description and data, and an output. The apparatus may also include a digital storage medium to store a library of predicted samples.

Disclosed in Taylor et al., U.S. Pat. No. 6,236,878, is a method for predictive modeling of human anatomy and physiologic function for planning medical interventions on at least one portion of a body with the goals of improving the outcome of the medical intervention and reducing the risks associated with medical intervention. The method comprises the steps of generation of multi-dimensional continuous geometric models of human anatomy, the generation of models of physiologic functions, the integration of the multi-dimensional continuous geometric human anatomy models with the physiologic functional models, and the use of the integrated models to predict the outcome of medical interventions. Also disclosed is a method for the integration of multi-dimensional continuous geometric models of human anatomy and models of physiologic functions to evaluate and predict changes in physiologic function in various functional states, stresses and environments and a method for generating data for disease research.

A method and apparatus for modeling circulation in a living subject is disclosed in Charbel et al, U.S. Pat. No. 7,191,110. The method includes the steps of developing a model for living subjects in general and correcting the model to substantially conform to the overall cerebral physiology of the living subject. The method further includes the step of calculating a cerebral flow of the living subject based upon the corrected model and a selected cerebral blood flow perturbation.

The paper by Spilker et al., Ann Biomed Eng (2007) 35:546-559. DOI 10.1007/s10439-006-9240-3, demonstrates the tuning of a model of pulmonary arterial hemodynamics with morphometry-based impedance outlet boundary conditions. A reduced-order model using steady flow was used to help initialize the tuning of a mean flow fraction and mean pressure of a more detailed model.

The paper by Ellwein et al., Cardiovasc Eng (2008) 8:73-87. DOI 10.1007/s10558-007-9050-8, describes a search for parameter values for unsteady cardiovascular simulations. This work involved tuning lumped-parameter models and, more specifically, models that were reduced to systems of ordinary differential equations (ODE's), which were solved with numerical methods for temporal integration of ODE's. An effort was made to identify the parameters to which the cardiovascular model was most sensitive.

This invention incorporates tuning of reduced-order models of unsteady cardiovascular dynamics and, in addition, reduced-order models that can be solved more quickly using Fourier analysis. In addition, this invention provides the framework for tuning features of time-varying hemodynamic simulations that allows the user to choose either a single objective function that combines many objectives, as in the work of Ellwein et al., or a set of objectives of the same size as the set of parameters so that a solution of a nonlinear system can be sought. This novel use of a limited set of features of the hemodynamic simulations as objectives can give the user control over the most important aspects of the simulation and may save computational energy.

A key difference between this invention and Kamm et al. U.S. Pat. No. 6,117,087, Taylor et al. U.S. Pat. No. 6,236,878, Charbel et al. U.S. Pat. No. 7,191,110, and the work of Ellwein et al. is this invention's use of these less detailed models in the process of tuning hemodynamic simulations that are significantly more computationally expensive. This difference makes this invention most valuable when implemented in software for modeling blood flow in three dimensions for the purposes of intervention planning, disease research and medical device design and evaluation. Previous work does not describe time-varying hemodynamic models of various degrees of complexity and their connection to one another. This aspect of this invention, along with the automation of the tuning process, will save users and computers significant time and effort.

SUMMARY OF THE INVENTION

Cardiovascular models have the potential to improve our understanding of the mechanics of the circulatory system in healthy and diseased states and to provide quantitative predictions of the outcomes of various interventions to aid in planning treatments. In order to serve this purpose, hemodynamic simulations must have the ability to faithfully represent a patient's circulation prior to treatment. Recent advances in the fidelity of hemodynamic simulations include the use of anatomic models constructed from medical image data, deformation of vascular walls, and improved representation of downstream vascular beds using appropriate outlet boundary conditions. This invention provides a method for employing these capabilities, enabling the systematic tuning of a hemodynamic simulation's parameters such that its hemodynamic characteristics match more than simply patient-specific vascular geometry, inlet flow, mean flow rates, and mean pressures.

DETAILED DESCRIPTION

The present invention applies computational methods to create cardiovascular simulations having desired hemodynamic features. A variety of cardiovascular modeling methods can be used to produce descriptions of time-varying blood flow and pressure in the heart and vascular networks. Numerical methods for optimization and solution of nonlinear systems of equations are used to find values for the parameters used in such models that result in simulations that match desired hemodynamic characteristics. These characteristics will often be those of the cardiovascular system of a particular subject. A variety of modeling methods are used for the same cardiovascular system such that more simplified models can be used to approximate the behavior of more detailed and complex models, which may lead to reduced computational expense. A system is created from these methods such that the user describes the desired features of the final cardiovascular simulation and provides minimal input, and the system automates the search for the final cardiovascular model.

Embodiments of this invention address cardiovascular models with a variety of parameters including, but not limited to, resistances, impedances, compliances, inductances, cardiac chamber elastances, material parameters of tissues, vascular network structures, and changes in these parameters with changes in physiological, disease, and interventional states. Also included are relationships between the various parameters of the models, including time constants defined by combinations of resistances and capacitors in lumped-parameter regions of cardiovascular models.

The desired features, called objectives, of the cardiovascular models addressed by embodiments of this invention include, but are not limited to, features of pressure waveforms, features of flow waveforms, features of time-varying velocity fields, features of transport, features of cardiac volume, features of tissue movements, and variations in these features with changes in physiological, disease, and interventional states. Relevant features of a time-varying quantity include the maximum, minimum, median, mean value over a certain portion of the cardiac cycle, and values at particular times.

The computational expense of solving the mathematical equations associated with a model of the cardiovascular system is generally related to the model's level of detail. The cost of solving these equations for several sets of values of a highly detailed model's parameters can be prohibitive. This motivates the approximation of a highly detailed model's behavior in a model that can be evaluated less expensively. For example, a numerical solution of the mechanics of blood flow and vascular motion in a three-dimensional arterial network with inlet boundary conditions representing the movement of the heart, outlet boundary conditions involving lumped-parameter models that approximate the behavior of downstream vascular networks, and deformable vessel walls has a high computational cost. This model's flow waveforms may be approximated, in an embodiment of this invention, by a lumped-parameter model that includes the inlet and outlet boundary conditions of the complex model and lumped-parameter models that approximate the impedances of the flow pathways from the inlet to the outlets, called intrinsic impedances. The reduced-order model allows testing many values for the lumped parameters of the inlet and outlet boundary conditions with low computational cost and can be used to help find a combination of these values that produces desired hemodynamic features in the highly detailed model. If the successful parameters of the lumped-parameter model do not meet the same success in the highly detailed model, the lumped-parameter model can be adjusted to contain more accurate intrinsic impedances. Other embodiments reduce the intrinsic impedances of the highly detailed model to impedance spectra in the reduced-order model.

Some embodiments of this method rely on less detailed models only to provide an initial estimate of the parameters of the more detailed models that will result in the desired hemodynamic features. Some embodiments use the less detailed models to determine the variations in cardiovascular model outputs with variations in parameter values.

The application of a preferred embodiment of this invention to the tuning of a specific model of blood flow in the abdominal aorta provides an illustrative example of the method disclosed herein. Patient-specific flow waveforms are measured in two locations, one proximal to the celiac bifurcation and one distal to the renal arteries. Maximum and minimum blood pressures are recorded. A detailed model is chosen, consisting of a geometric model of the abdominal aorta and its largest branch vessels, created from medical image data, a highly refined mesh of the geometric model on which the incompressible Navier-Stokes equations are solved in three-dimensions using a finite element method. Vessel wall deformations are modeled. Measured flow is applied at the inlet, and outlet boundary conditions are impedances of three-element windkessel lumped-parameter models. The objectives are the desired maximum, minimum, and median of the pressure waveform, the amplitude and diastolic mean value of the measured infrarenal flow waveform, and the mean flow through the infrarenal plane. A set of parameters is chosen by varying several sets of parameters and observing the resulting changes in flow and pressure waveforms. The model parameters chosen to be tuned are the total resistance of the outlets proximal to the infrarenal plane, the total resistance of the distal outlets, and mean values and ratios of the values of the following two quantities for the three-element windkessels proximal and distal to the plane: the ratio of the proximal resistor to the total resistance and the time constant, defined by the product of the capacitance and the distal resistance. Resistances of the outlet vessels are determined by the total resistance of the region to which they belong and the approximate mean flow fractions found in the literature. The tuning of the boundary condition parameters is formulated as a system of six nonlinear equations in six unknowns, seeking a root where the simulated and measured hemodynamic conditions match. This nonlinear system is solved using a quasi-Newton method where each function evaluation requires one three-dimensional simulation. The Jacobian of this system is updated using a version of Broyden's method in which attention is paid to scaling of the different parameters to distribute the secant updates appropriately. The objectives are evaluated first using a reduced-order model consisting of the impedances of the three-element windkessels in parallel. This lumped-parameter model is solved to determine the initial boundary condition parameters for the three-dimensional model. Three-dimensional simulations are run on a coarse initial mesh with a boundary layer at the vessel wall. When a solution of this model is found, the mesh is further refined, more boundary layers are added, and the tuning continues until the simulation on an adequately refined mesh matches the objectives to a desired tolerance. This example illustrates the tuning of parameters that are related to resistances and capacitances. It also illustrates the use of a lumped-parameter model as a reduced-order model for the more detailed cardiovascular model.

This invention employs a range of levels of detail in cardiovascular models. One possible increase in the level of detail is a change from a model using prescribed flow in a blood vessel to a model using an elastance-based model of a cardiac chamber. This allows the prediction of the reaction of the heart to changes in afterload. Another possible increase in the level of detail comes with a change from a model that can be described by a system of ordinary differential equations that can be solved with Fourier analysis to a model that can be described by a system of ordinary differential equations that must be solved with numerical methods for temporal integration. This may occur when a cardiovascular model with an elastance-based heart model is desired. Increases in the level of detail of cardiovascular models also are associated with a change from a model assuming rigid vascular walls to a model assuming more realistic representations of these walls and, in numerical solutions of partial differential equations governing the cardiovascular system, increasingly refined computational meshes and increasingly complete polynomial bases.

Figure 1:
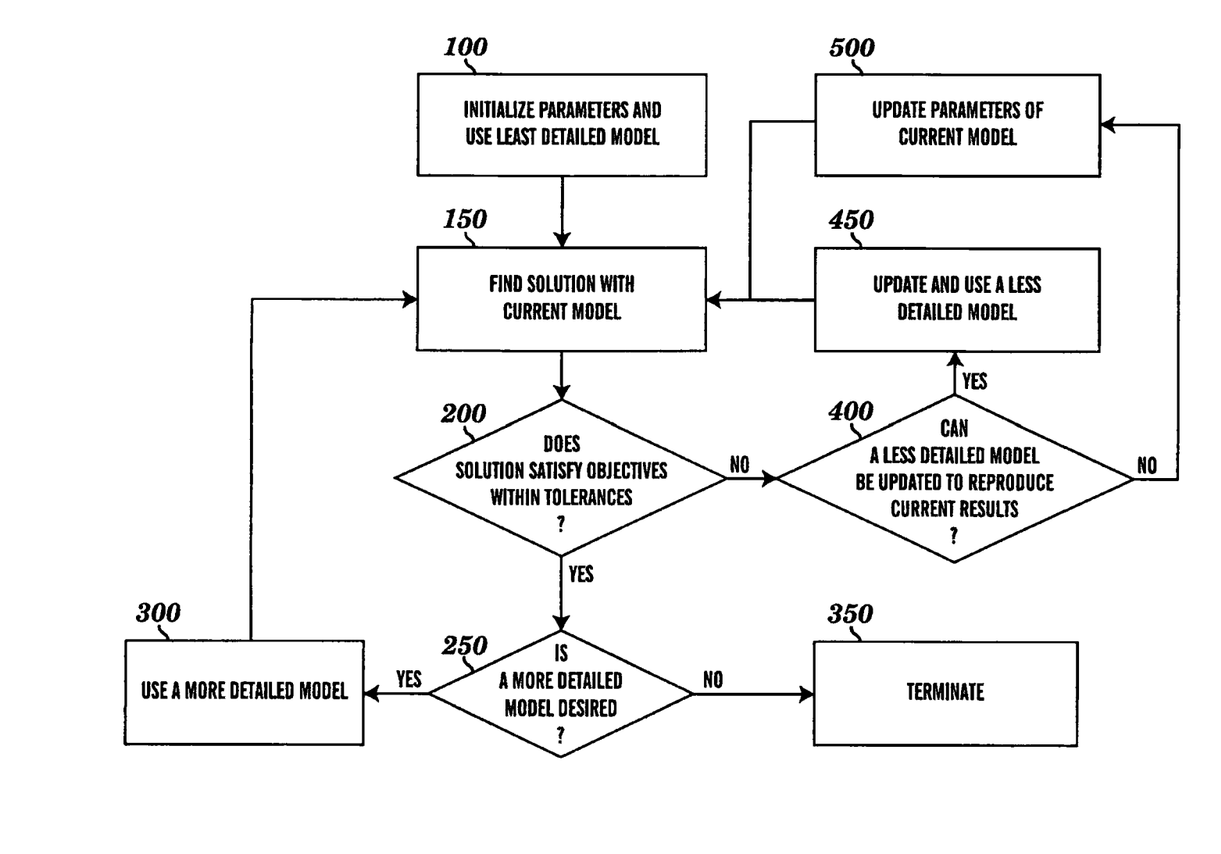
FIG. 1 is a flow chart illustrating an embodiment of the method of the present invention for tuning patient-specific hemodynamic simulations.

The steps in a preferred embodiment of the method for tuning patient-specific hemodynamic simulations are shown in FIG. 1. The parameters for the least detailed model of the cardiovascular system are initialized 100. This step can be aided by prior knowledge of ranges of values for each parameter of such a model. Next, the solution of the mathematical equations governing the current model is sought 150. This includes the determination of the change in the model's features with changes in the model's parameters. A first determination 200 is made if the solution satisfies the objectives within tolerances. If it does, then a second determination 250 is made if a more detailed model is desired. If one is not, then the method has reached a final solution 350. If the second determination 250 is that a more complex model is needed, then a second model 300 is used wherein the level of detail of the second model is increased. The more complex second model 300 is then solved 150 and the process repeated. If the first determination 200 does not satisfy the objectives within tolerances, a third determination 400 is made if a less detailed model can be updated to reproduce current results. If it can, a third model with a reduced level of detail is updated 450 such that it reproduces, within a reasonable tolerance, the important aspects of the more detailed model's results. The less detailed model is then solved 150. If the third determination 400 is that a less detailed model cannot be updated to reproduce current results, then a new model 500 is created by updating the parameters of the current model 150, and the method is repeated until the method has reached a final solution 350.

In a related embodiment of this invention, a less detailed model that approximates the results of a more detailed cardiovascular model is produced as the final result of the tuning procedure. Less detailed models can be used to succinctly characterize cardiovascular systems and in applications requiring rapid simulations, such as the study of relationships between a model's parameters and its behavior.

Some embodiments of this invention involve evaluation of the appropriateness of parameter sets for achieving objectives of cardiovascular dynamics. Certain sets of parameters are associated with better performance of tuning procedures. Parameter sets to which all components of the objective functions are adequately sensitive are desired. Evaluation of various parameter sets can be performed quickly using representative models with less detail.

This invention solves the problem of making cardiovascular simulations match desired hemodynamic characteristics without excessive and ad hoc user interactions. Systematic tuning is enabled by the formulation of one of several problems. A single objective function can be chosen to summarize the differences between the desired and current features of the cardiovascular model. Embodiments with such a cost function employ optimization methods that minimize this difference. In other embodiments having the same number of parameters as objectives, a solution of a system of nonlinear equations is sought. In other embodiments, a solution of a nonlinear least-squares problem is sought. Numerical methods for solving each of these problems are chosen such that the number of function evaluations is kept low. Finite-difference evaluations of Hessian and Jacobian matrices are reduced, in some embodiments, by use of secant updates. Estimates of these matrices are created, in some embodiments, using evaluations of less detailed models.

Highly detailed cardiovascular models may require the use of lumped parameters to represent regions of the cardiovascular system. To aid in the process of choosing parameters for these models without repeated calculation, an embodiment of this invention determines relationships between lumped parameter values and parameters of more detailed distributed cardiovascular models by approximating these more detailed models with lumped-parameter models. The derived relationships can be stored and used by other embodiments to save computational effort.

Several embodiments of the present invention involve analysis of variations of the parameters of cardiovascular models. Patient-specific measurements have natural variations and, when associated with tuned sets of parameters, can provide succinct information about variability of the individual's cardiovascular system. Members of a class of patients can likewise be analyzed for variability within that class of patients. Related embodiments use such information on variability to analyze ranges of potential outcomes of treatments.

The present invention improves upon existing methods by providing a framework for creating state-of-the-art, detailed cardiovascular models that have desired hemodynamic characteristics with methods that automate the procedure and seek to minimize the computational effort. Existing methods use simplified mathematical models or seek to match only temporal mean values of time-varying quantities. Automation of the process allows users to request features of pressure, flow, vascular motion, cardiac motion, and other physiological data and, after providing anatomic and physiological information for the desired cardiovascular model, take no further action while the system produces a mathematical vascular model with the requested results. This capability enables the creation of patient-specific simulations and predictions of the cardiovascular response to various treatments.

Variations can be created from the general approach defined herein. A variety of cardiovascular modeling methods can be used to create the models with various levels of detail and simplifying assumptions. A variety of numerical methods can be used to tune parameters of the cardiovascular models. A variety of sets of hemodynamic objectives and parameters can also be chosen. A variety of algorithms can be chosen to link models of various levels of detail.

In surgical treatment planning, this invention can be used to create cardiovascular models that match hemodynamic features of a specific patient before predicting the results of a variety of surgical options. In medical device development, this invention can be used to create cardiovascular models that match a variety of possible physiological situations to use in simulating the effects of devices on blood flow and pressure or the forces acting on devices that might affect their short-term and long-term safety and efficacy. In cardiovascular tissue engineering, this invention can be used to create cardiovascular models with realistic pressure, flow, and deformation to develop an understanding of the biomechanical environment of tissues.

The present invention allows the user to predict hemodynamic results of interventions without expensive biological experiments thereby reducing user interaction time and computational expense to create realistic cardiovascular models.

We claim:

1. A computer system for determining cardiovascular information from patient-specific image data, to predict a hemodynamic result of a medical intervention for a patient, the computer system comprising:
    a data storage device storing received patient-specific image data and instructions for processing the received patient-specific image data for determining cardiovascular information including predictions of hemodynamic results for a patient; and
    a processing device configured to execute the stored instructions for processing the received patient-specific image data, the instructions executing a method comprising:
        receiving patient-specific image data regarding a geometry of an anatomical structure of the patient;
        creating, based on the patient-specific image data, a three-dimensional model representing at least a portion of the anatomical structure of the patient, the three-dimensional model including portions representing at least one inlet and at least one outlet of blood flow;
        determining one or more boundary condition parameters for at least one of the at least one inlet or the at least one outlet of the three-dimensional model;
        executing, using the at least one computer system, a three-dimensional simulation on the three-dimensional model, based on the determined one or more boundary condition parameters, to determine a blood flow characteristic within the anatomical structure of the patient;
        creating, based on the executed three-dimensional simulation, a reduced-order model that is computationally faster than the three-dimensional model and that represents at least part of the portion of the anatomical structure of the patient represented by the three-dimensional model;
        determining a medical intervention to be simulated using the reduced-order model; and
        predicting a hemodynamic result of the medical intervention for the patient by solving the reduced-order model to determine an update to the blood flow characteristic.

2. The computer system of claim 1, wherein the reduced-order model reproduces, within a tolerance, the blood flow characteristic determined using the three-dimensional model.

3. The computer system of claim 1, wherein the processing device is further configured to determine the blood flow characteristic within the anatomical structure of the patient using the reduced order model.

4. The computer system of claim 3, wherein the processing device is further configured to:
    compare the blood flow characteristic determined using the three-dimensional model with the blood flow characteristic determined using the reduced-order model; and
    determine whether to adjust the reduced-order model based on the comparison.

5. The computer system of claim 4, wherein the processing device is further configured to determine whether to adjust the reduced-order model based on whether differences between the blood flow characteristic determined using the three-dimensional model and the blood flow characteristic determined using the reduced-order model are outside a tolerance.

6. The computer system of claim 5, wherein the processing device is further configured to adjust the reduced-order model by increasing the level of detail of the reduced-order model when the differences are outside the tolerance.

7. The computer system of claim 4, wherein the processing device is further configured to adjust the reduced-order model by adjusting the level of detail of the reduced-order model.

8. The computer system of claim 1, wherein the processing device is further configured to determine whether to adjust the reduced-order model to include a lower level of detail while reproducing, within a tolerance, the blood flow characteristic determined using the three-dimensional model.

9. The computer system of claim 1, wherein:
    the three-dimensional model includes a three-dimensional mesh; and
    the reduced-order model has less than three dimensions.

10. The computer system of claim 1, wherein:
    the three-dimensional model includes a three-dimensional mesh; and
    the reduced-order model is created based on a mesh that is less refined than the three-dimensional mesh.

11. The computer system of claim 1, wherein the processing device is further configured to determine the blood flow characteristic within the anatomical structure of the patient by solving equations governing blood flow using the reduced-order model, the initial blood flow model being associated with a more complete polynomial basis for solving the equations governing blood flow than the reduced-order model.

12. The computer system of claim 1, wherein:
    the initial boundary condition parameters represent flow in the at least one blood vessel using an elastance-based model of the patient's cardiac chamber; and
    the reduced-order model includes a prescribed flow in the at least one blood vessel in the anatomical structure of the patient.

13. The computer system of claim 1, wherein the processing device is further configured to:
    determine the blood flow characteristic by solving a system of differential equations with numerical methods for temporal integration using the initial boundary condition parameters; and
    determine the blood flow characteristic by solving a system of differential equations with Fourier analysis using the reduced-order model.

14. The computer system of claim 1, wherein the reduced-order model includes a model assuming vascular walls that are more rigid than the corresponding vascular walls of the initial blood flow model.

15. The computer system of claim 1, wherein:
the initial boundary condition parameters are associated with a model assuming rigid vascular walls; and
the reduced-order model includes a model assuming vascular walls that are less rigid than the corresponding vascular walls associated with the initial boundary condition parameters.

16. The computer system of claim 1, wherein:
the anatomical structure includes at least a portion of a plurality of coronary arteries emanating from the aorta; and
the portion of the anatomical structure represented by the three-dimensional model includes at least a portion of the plurality of coronary arteries, the three-dimensional model representing at least one fluid flow inlet and at least one fluid flow outlet.

17. The computer system of claim 1, wherein the blood flow characteristic includes at least one of blood flow or pressure within the anatomical structure of the patient.

18. A computer-implemented method for determining cardiovascular information from patient-specific image data to predict a hemodynamic result of a medical intervention for a patient using at least one computer system, the method comprising:
receiving, at the at least one computer system, patient-specific image data regarding a geometry of an anatomical structure of the patient;
creating, using the at least one computer system and based on the patient-specific image data, a three-dimensional model representing at least a portion of the anatomical structure of the patient, the three-dimensional model including portions representing at least one inlet and at least one outlet for blood flow;
determining one or more boundary condition parameters for the at least one of the at least one inlet or the at least one outlet of the three-dimensional model;
executing, using the at least one computer system, a three-dimensional simulation on the three-dimensional model, based on the determined one or more boundary condition parameters, to determine a blood flow characteristic within the anatomical structure of the patient;
creating, based on the executed three-dimensional simulation, a reduced-order model that is computationally faster than the three-dimensional model and that represents at least part of the portion of the anatomical structure of the patient represented by the three-dimensional model;
determining a medical intervention to be simulated using the reduced-order model; and
predicting a hemodynamic result of the medical intervention for the patient by solving the reduced-order model to determine an update to the blood flow characteristic.

19. The method of claim 18, wherein the reduced-order model reproduces, within a tolerance, the blood flow characteristic determined using the three-dimensional model.

20. The method of claim 18, further including determining, using the at least one computer system, the blood flow characteristic within the anatomical structure of the patient using the reduced-order model.

21. A non-transitory computer readable medium for use on at least one computer system containing computer-executable programming instructions for performing a method for determining patient-specific cardiovascular information from received patient-specific image data to predict a hemodynamic result of a medical intervention for a patient, the method comprising:
receiving patient-specific image data regarding a geometry of an anatomical structure of the patient;
creating, based on the patient-specific image data, a three-dimensional model representing at least a portion of the anatomical structure of the patient, the three-dimensional model including portions representing at least one inlet and at least one outlet for blood flow;
determining one or more boundary condition parameters for the three-dimensional model for the at least one inlet or at least one outlet of the three-dimensional model;
executing, using the at least one computer system, a three-dimensional simulation on the three-dimensional model, based on the determined one or more boundary condition parameters, to determine a blood flow characteristic within the anatomical structure of the patient;
creating, based on the executed three-dimensional simulation, a reduced-order model that is computationally faster than the three-dimensional model and that represents at least part of the portion of the anatomical structure of the patient represented by the three-dimensional model;
determining a medical intervention to be simulated using the reduced-order model; and
predicting a hemodynamic result of the medical intervention for the patient by solving the reduced-order model to determine an update to the blood flow characteristic.

22. The non-transitory computer readable medium of claim 21, wherein the reduced-order model reproduces, within a tolerance, the blood flow characteristic determined using the three-dimensional model.

23. The non-transitory computer readable medium of claim 22, the method further including determining, using the at least one computer system, the blood flow characteristic within the anatomical structure of the patient using the reduced-order model.

24. The non-transitory computer readable medium of claim 23, the method further including:
comparing the blood flow characteristic determined using the three-dimensional model with the blood flow characteristic determined using the reduced-order model; and
determining whether to adjust the reduced-order model based on the comparison.

25. The non-transitory computer readable medium of claim 24, the method further including:
determining whether to adjust the reduced-order model based on whether differences between the blood flow characteristic determined using the three-dimensional model and the blood flow characteristic determined using the reduced-order model are outside a tolerance.

* * * * *